United States Patent
Blanz et al.

(10) Patent No.: US 9,121,966 B2
(45) Date of Patent: Sep. 1, 2015

(54) MEDIA DISPLACEMENT DEVICE AND METHOD OF IMPROVING TRANSFER OF ELECTROMAGNETIC ENERGY BETWEEN A TOOL AND AN EARTH FORMATION

(75) Inventors: Martin Blanz, Celle (DE); Christoph Meyer, Scharnhorst (DE); Thomas Kruspe, Wietzendorf (DE); Holger Tietjen, Hannover (DE)

(73) Assignee: Baker Hughes Incorporated, Houston, TX (US)

( * ) Notice: Subject to any disclaimer, the term of this patent is extended or adjusted under 35 U.S.C. 154(b) by 658 days.

(21) Appl. No.: 13/305,424

(22) Filed: Nov. 28, 2011

(65) Prior Publication Data

US 2013/0134971 A1 May 30, 2013

(51) Int. Cl.
*G01V 3/32* (2006.01)
*G01N 24/08* (2006.01)

(52) U.S. Cl.
CPC ............ *G01V 3/32* (2013.01); *G01N 24/081* (2013.01)

(58) Field of Classification Search
CPC .............................. G01V 3/32; G01N 24/081
See application file for complete search history.

(56) References Cited

U.S. PATENT DOCUMENTS

| | | | | |
|---|---|---|---|---|
| 3,167,707 A | * | 1/1965 | Oliver | 324/347 |
| 3,390,737 A | * | 7/1968 | Johnson | 181/106 |
| 3,503,038 A | * | 3/1970 | Baldwin | 367/25 |
| 4,933,638 A | | 6/1990 | Kleinberg et al. | |
| 4,974,446 A | * | 12/1990 | Vigneaux | 73/152.42 |
| 4,982,381 A | * | 1/1991 | Mari | 367/27 |
| 5,005,422 A | * | 4/1991 | Ruscev et al. | 73/784 |
| 5,036,916 A | * | 8/1991 | Bennett | 166/253.1 |
| 5,052,220 A | * | 10/1991 | Piers | 73/152.36 |
| 5,280,243 A | | 1/1994 | Miller | |
| 5,408,097 A | * | 4/1995 | Wraight et al. | 250/256 |
| 5,432,446 A | | 7/1995 | MacInnis et al. | |
| 5,610,522 A | | 3/1997 | Locatelli et al. | |
| 5,631,563 A | | 5/1997 | Moriarty | |
| 5,646,528 A | | 7/1997 | Hanley | |
| 5,767,674 A | | 6/1998 | Griffin et al. | |
| 5,794,703 A | * | 8/1998 | Newman et al. | 166/381 |
| 5,939,717 A | * | 8/1999 | Mullins | 250/255 |
| 5,992,468 A | * | 11/1999 | Dwiggins | 138/108 |
| 6,018,243 A | | 1/2000 | Taicher et al. | |
| 6,082,461 A | * | 7/2000 | Newman et al. | 166/381 |
| 6,089,323 A | * | 7/2000 | Newman et al. | 166/381 |
| 6,138,756 A | * | 10/2000 | Dale | 166/254.2 |

(Continued)

FOREIGN PATENT DOCUMENTS

| | | |
|---|---|---|
| EP | 1072903 A1 | 1/2001 |
| WO | 03048811 | 6/2003 |

OTHER PUBLICATIONS

B.R.De et al., "Ultrabroadband electromagnetic Well Logging: A Potential Future Technology"; SPWLA 33rd Annual Logging Symposium, Jun. 14-17, 1992; 23 pages.

(Continued)

*Primary Examiner* — Dixomara Vargas
(74) *Attorney, Agent, or Firm* — Cantor Colburn LLP

(57) ABSTRACT

A media displacement device has a body configured to be positioned radially outwards of a tool having an antenna for transmitting electromagnetic energy to or receiving electromagnetic energy from an earth formation. The body is made of materials causing less power loss to electromagnetic energy transmitted or received by the tool than the media the body is configured to displace.

19 Claims, 6 Drawing Sheets

(56) References Cited

U.S. PATENT DOCUMENTS

| | | | |
|---|---|---|---|
| 6,170,601 B1 * | 1/2001 | Nakajima et al. | 181/102 |
| 6,179,055 B1 * | 1/2001 | Sallwasser et al. | 166/254.2 |
| 6,246,236 B1 | 6/2001 | Poitzsch et al. | |
| 6,315,075 B1 * | 11/2001 | Nakajima | 181/102 |
| 6,348,792 B1 * | 2/2002 | Beard et al. | 324/303 |
| 6,445,180 B1 | 9/2002 | Reiderman et al. | |
| 6,459,263 B2 * | 10/2002 | Hawkes et al. | 324/303 |
| 6,580,273 B2 | 6/2003 | Reiderman et al. | |
| 6,667,620 B2 | 12/2003 | Homan et al. | |
| 6,827,148 B2 * | 12/2004 | Shaw et al. | 166/381 |
| 6,838,876 B2 | 1/2005 | Kruspe et al. | |
| 6,898,967 B2 * | 5/2005 | Macpherson | 73/152.05 |
| 6,915,875 B2 | 7/2005 | Dubinsky et al. | |
| 6,920,936 B2 * | 7/2005 | Sheiretov et al. | 166/382 |
| 6,995,684 B2 | 2/2006 | Clark | |
| 6,997,258 B2 | 2/2006 | Homan et al. | |
| 7,168,508 B2 | 1/2007 | Goldberg et al. | |
| 7,246,660 B2 * | 7/2007 | Fripp et al. | 166/65.1 |
| 7,334,642 B2 * | 2/2008 | Doering et al. | 166/382 |
| 7,431,080 B2 * | 10/2008 | Wright et al. | 166/210 |
| 7,463,027 B2 | 12/2008 | Prammer et al. | |
| 7,516,782 B2 * | 4/2009 | Sheiretov et al. | 166/206 |
| 7,778,778 B2 * | 8/2010 | Bespalov et al. | 702/7 |
| 7,854,258 B2 * | 12/2010 | Sheiretov et al. | 166/98 |
| 8,015,868 B2 * | 9/2011 | Hassan et al. | 73/152.46 |
| 8,354,846 B2 * | 1/2013 | Forgang et al. | 324/339 |
| 8,393,874 B2 * | 3/2013 | Zazovsky et al. | 417/16 |
| 8,479,820 B2 * | 7/2013 | Kaul et al. | 166/302 |
| 2001/0045829 A1 | 11/2001 | Prammer et al. | |
| 2003/0006766 A1 | 1/2003 | Kruspe et al. | |
| 2006/0260864 A1 | 11/2006 | Egerev et al. | |

OTHER PUBLICATIONS

R.J. Gilmore, et al., "Enhanced Saturation Determination Using the EPT-G Endfire Antenna Array"; SPWLA Twenty-Eighth Annual Logging Symposium, Jun. 29, 1987; 24 pages.

Salvador Rodriguez et al., "Reservoir Monitoring Using Permanent Sources and Vertical Receiver Antennae: The Cere-la-Ronde Case Study"; Institut francais du Petrole, France; Block 1, Forum 4, Rio de Janeiro, Brazil; Sep. 1, 2002; pp. 383-392.

Notification of the International Search Report and the Written Opinion of the International Searching Authority; PCT/US2012/064624; Mailed Mar. 29, 2013; Korean Intellectual Property Office; 8 pages.

* cited by examiner

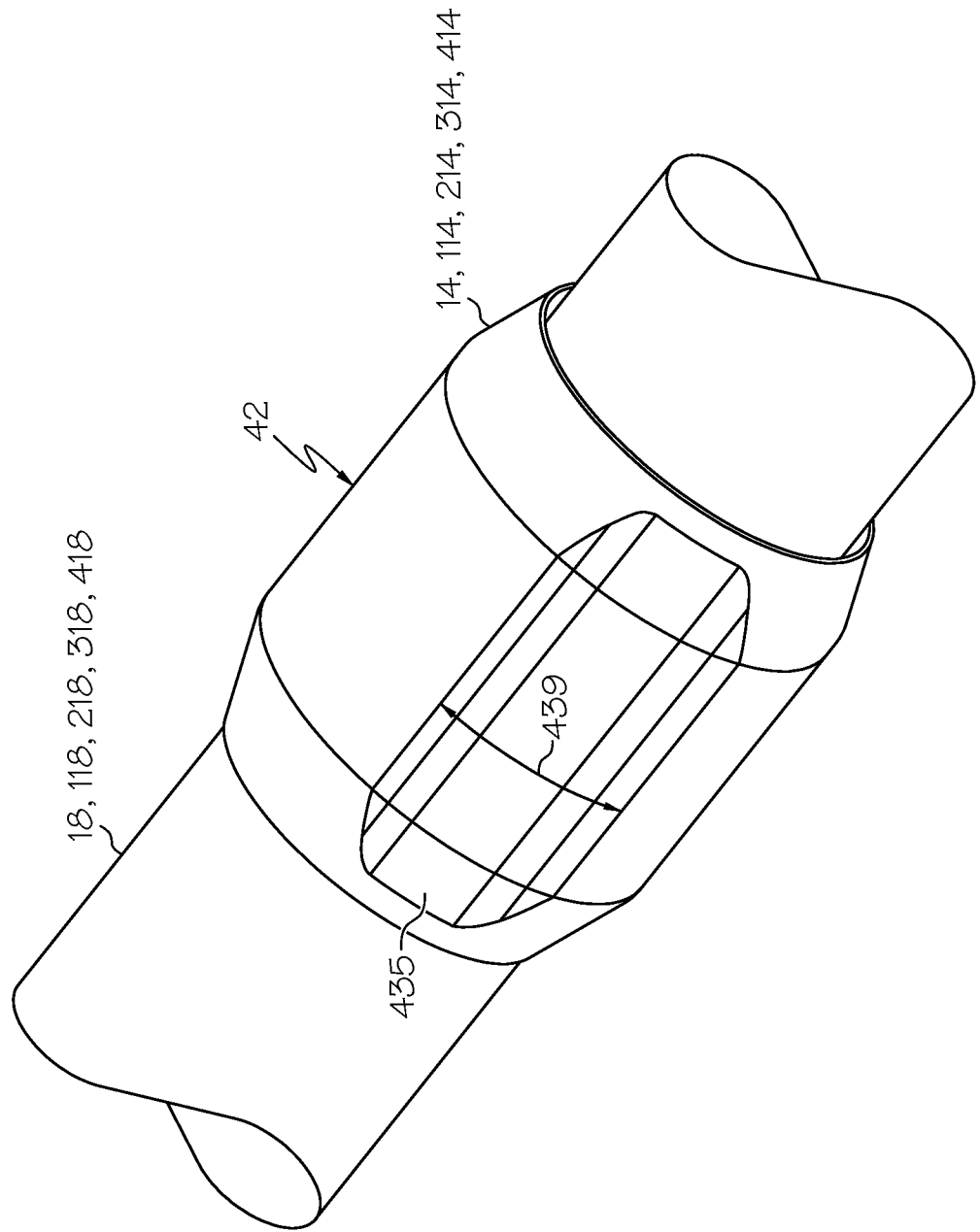

MEDIA DISPLACEMENT DEVICE AND METHOD OF IMPROVING TRANSFER OF ELECTROMAGNETIC ENERGY BETWEEN A TOOL AND AN EARTH FORMATION

BACKGROUND

Systems that employ electromagnetic energy for monitoring or imaging, such as NMR (Nuclear Magnetic Resonance) and inductive resistivity logging, for example, rely on transmission and reception of electromagnetic energy. Such systems are used in the downhole industry where NMR tools are positioned within a borehole for formation evaluation. An antenna within the NMR tool is configured to transmit electromagnetic energy into and receive it from the formation being queried. Any extra media that impedes efficient transfer of electromagnetic energy between the antenna and the formation has a negative effect on performance of the system. New systems and methods that increase the efficiency of the aforementioned energy transfer are always well received in the art.

BRIEF DESCRIPTION

Disclosed herein is a media displacement device having a body configured to be positioned radially outwards of a tool having an antenna for transmitting electromagnetic energy to or receiving electromagnetic energy from an earth formation. The body is made of materials causing less power loss to electromagnetic energy transmitted or received by the tool than the media the body is configured to displace.

Further disclosed herein is a method of improving transfer of electromagnetic energy between a tool and an earth formation. The method includes, selecting one of a plurality of selectable electromagnetic energy transmitting or receiving tools having outer radial dimensions smaller than radial dimensions of a borehole at a location of the borehole where the selected tool will be positioned, selecting one of a plurality of selectable media displacement devices having internal radial dimensions complementary to the outer radial dimensions of the selected tool and external radial dimensions less than the radial dimensions of the borehole at the location where the selected tool will be positioned, and attaching the selected one of the plurality of selectable media displacement devices to the selected tool.

BRIEF DESCRIPTION OF THE DRAWINGS

The following descriptions should not be considered limiting in any way. With reference to the accompanying drawings, like elements are numbered alike:

FIG. 6 depicts a perspective view of a feature employable in any of the media displacement devices disclosed herein.

DETAILED DESCRIPTION

A detailed description of one or more embodiments of the disclosed apparatus and method are presented herein by way of exemplification and not limitation with reference to the Figures.

Figure 1:
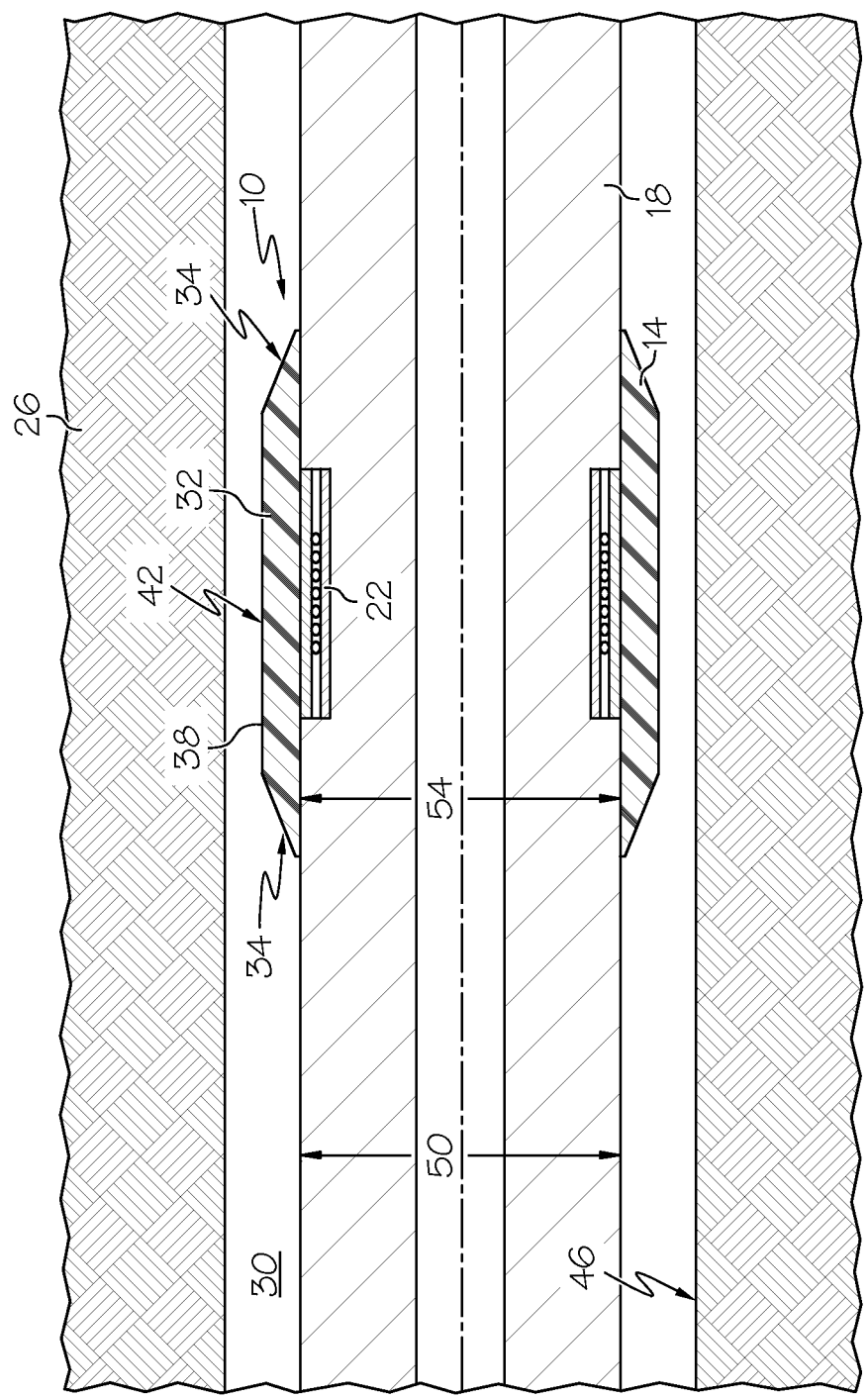
FIG. 1 depicts a cross sectional view of a media displacement device disclosed herein.

Referring to FIG. 1, an embodiment of a media displacement device disclosed herein is illustrated at 10. The device 10 includes, a body 14 positionable radially outwardly of a tool 18 having an antenna 22. In this embodiment the antenna 22 is configured and adapted to transmit electromagnetic energy into an earth formation 26 as well as receive electromagnetic energy from the earth formation 26, such as is used for nuclear magnetic resonance (NMR) in the downhole industry, for example. The body 14 is positioned and configured to displace media 30, such as drilling mud, for example that could otherwise negatively affect electromagnetic energy being transmitted from or received by the antenna 22. This negative affect could be due to electrical conductivity of the media 30 resulting in power loss of electromagnetic energy transmitted through media 30. By making the body 14 of materials that are less conductive than the media 30, such as polymer, for example, the electromagnetic energy is able to pass through the body 14 with less power loss than if it were to pass through the media 30 directly.

The body 14, in this illustrated embodiment, has a cylindrical center portion 32 with longitudinal ends 34 that taper in radial thickness. The center portion 32 has a longitudinal dimension substantially equal to or greater than that of the antenna 22. The body 14 is constructed of materials having low conductivity such as rubbers or other polymers, ceramics, glass and combinations of these. Additionally, the body could include pieces of metal to provide structural support thereto. The pieces of metal could be small particles, such as slivers, dispersed within the body 14, or could be strips 38 positioned along the maximum radial surface 42 of the body 14. The strips 38 could provide additional resistance against mechanical damage to the body 14 during running into and out of a borehole 46, for example. By using a metal with high electrical conductivity for the pieces or the strips 38 the power loss to the electromagnetic energy passing therethrough can be minimized. Hard copper alloys such as copper beryllium are good candidates for the metal pieces. Additionally, the pieces or the strips 38 can be sized, positioned and oriented relative to the antenna 22 to minimize any negative impact on the transmission and reception between the antenna 22 and the formation 26.

Dimensionally the body 14 should be sized to displace as much volume of the media 30 that exists between the antenna 22 and the formation 26 as is practical in each application. It is likely that specific variations of the tool 18 are already available in select sizes defined at least in part by outer radial dimensions 50. Fabricating new versions of the tool 18 with customized values of the outer radial dimension 50 is not practical from a cost versus benefit stand point. However, fabricating a plurality of the media displacement devices 10 with the bodies 14 having interior radial dimensions 54 that complement the outer radial dimensions 50 of the available tools 18 and selectable maximum radial surfaces 42 is likely to be cost effective. With the devices 10 available, an operator can select one of the plurality of bodies 14 that is sized to complement the tool 18 being deployed and having the maximum radial surface 42 that fits within the borehole 46 while not leaving excessive radial clearance therebetween, which media 30 could occupy.

Several embodiments employing differing methods of attachment of the body 14 to the tool 18 are described hereunder. The embodiment of the device 10 illustrated in FIG. 1 employs a frictional engagement between the interior radial dimension 54 of the body 14 and the outer radial dimension 50 of the tool 18. This frictional engagement can be enhanced with adhesive applied to one or both surfaces defined by the dimensions 50, 54 as well as by swelling of the body 14 that causes the interior radial dimension 54 thereof to shrink thereby increasing frictional engagement with the tool 18.

Figure 2:
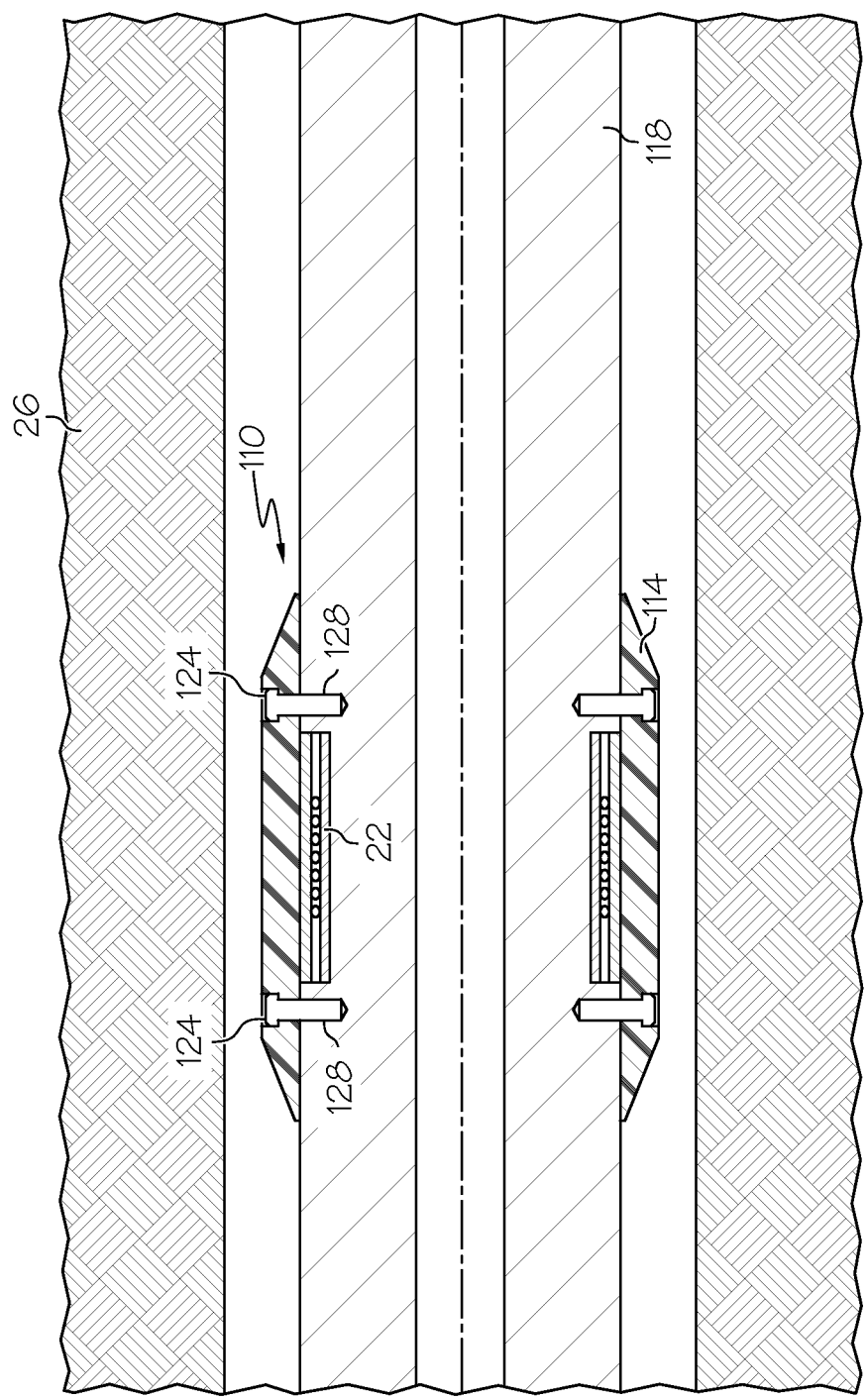
FIG. 2 depicts a cross sectional view of one embodiment of a media displacement device disclosed herein.

Referring to FIG. 2, an alternate embodiment of a media displacement device disclosed herein is illustrated at 110. The device 110 is similar to the device 10 and therefore only the differences between the two will be described hereunder. The device 110 differs from the device 10 in how body 114 is attached to a tool 118. A plurality of fasteners 124, shown herein as screws, threadably engages in holes 128 in the tool 118 to fixedly attach the body 114 to the tool 118. Any desirable number of the fasteners 124 could be employed to assure the body 114 remains fixed to the tool 118.

Figure 3:
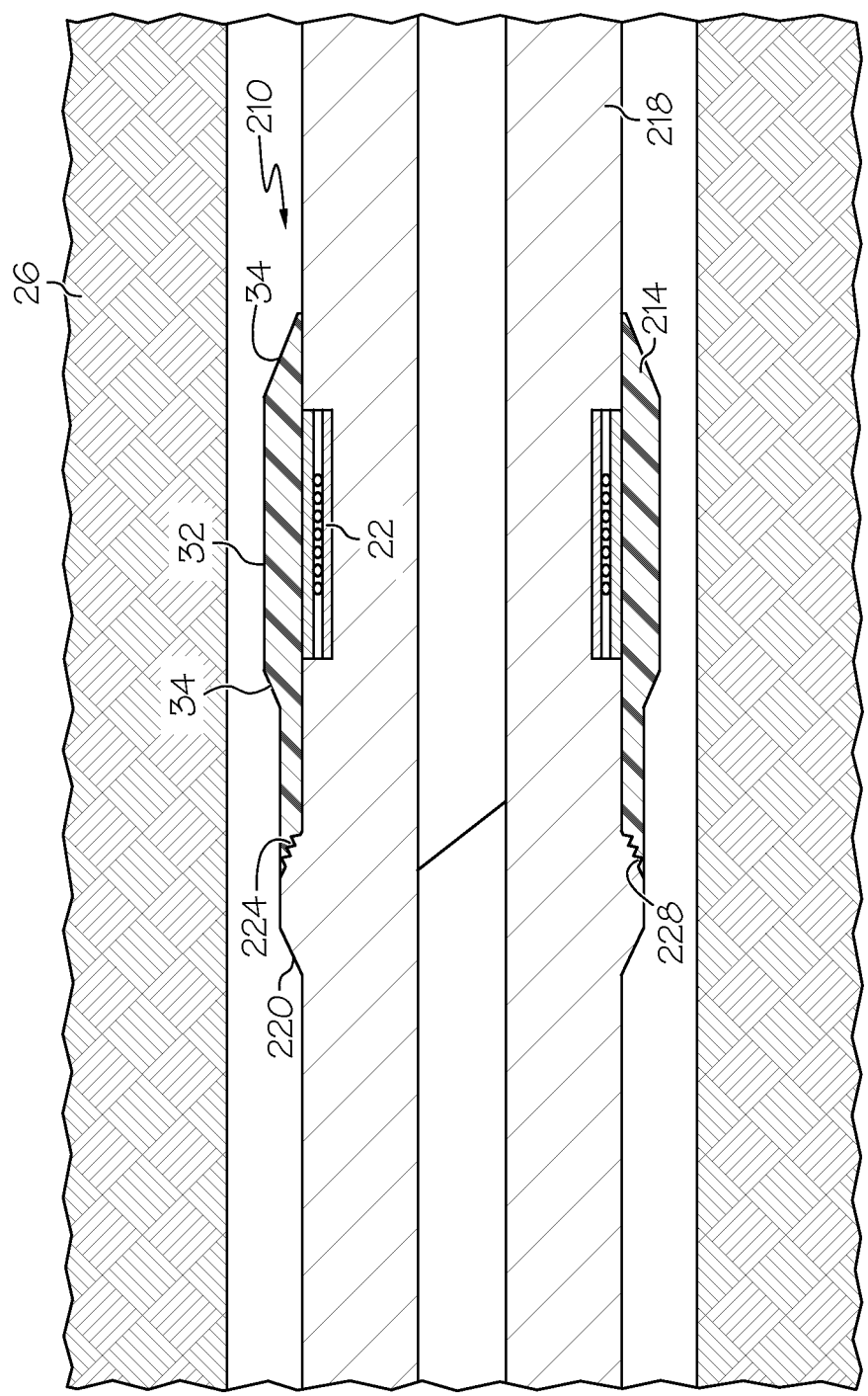
FIG. 3 depicts a cross sectional view of another embodiment of a media displacement device disclosed herein.

Referring to FIG. 3, another alternate embodiment of a media displacement device disclosed herein is illustrated at 210. Again, only the differences between the device 210 and the device 10 will be elaborated on herebelow. The device 210 differs from the device 10 in how body 214 is attached to a tool 218. A sleeve portion 220 of the tool 218 has threads 224 that threadably engage with threads 228 on the body 214. This threadable engagement fixes the cylindrical center portion 32 of the body 214 directly radially of the antenna 22. By positioning the sleeve portion 220 longitudinally beyond a longitudinal end 34 of the center portion 32 the sleeve portion 220 can be made of any desirable material without concern that it will negatively affect the energy transfer between the antenna 22 and the formation 26.

Figure 4:
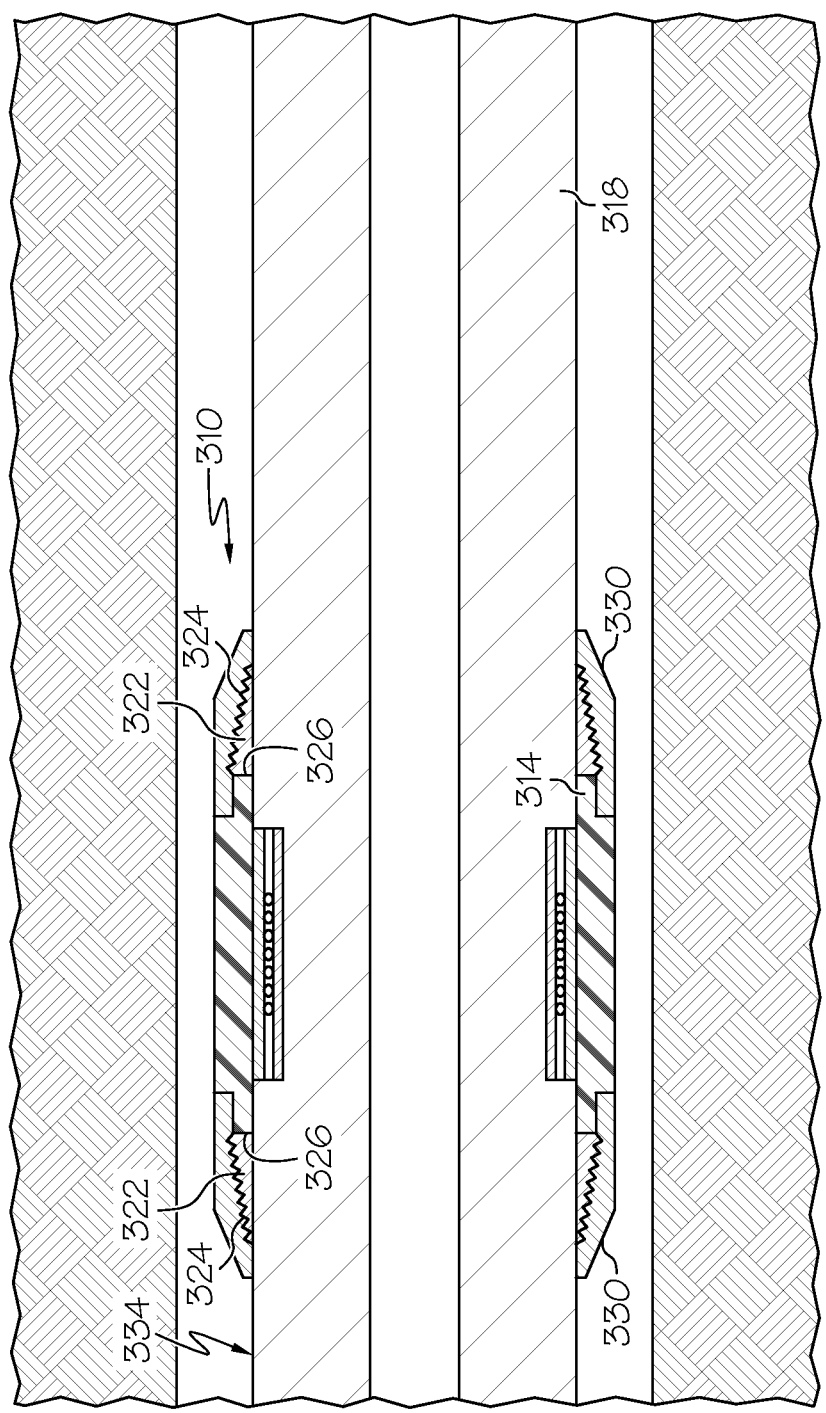
FIG. 4 depicts a cross sectional view of another embodiment of a media displacement device disclosed herein.

Referring to FIG. 4, another alternate embodiment of a media displacement device disclosed herein is illustrated at 310. Again, only the differences between the device 310 and the device 10 will be elaborated on herebelow. The device 310 differs from the device 10 in how body 314 is attached to a tool 318. Split parts 322 having tapered threads 324 are abutted to either longitudinal end 326 of the body 314. A pair of collars 330 are threadably engagable with the tapered threads 324 of the split parts 322. Threadably tightening the collars 330 onto the split parts 322 to cause the split parts 322 to become frictional engaged with an outer surface 334 of the tool 318 to thereby fix the body 314 to the tool 318.

Figure 5:
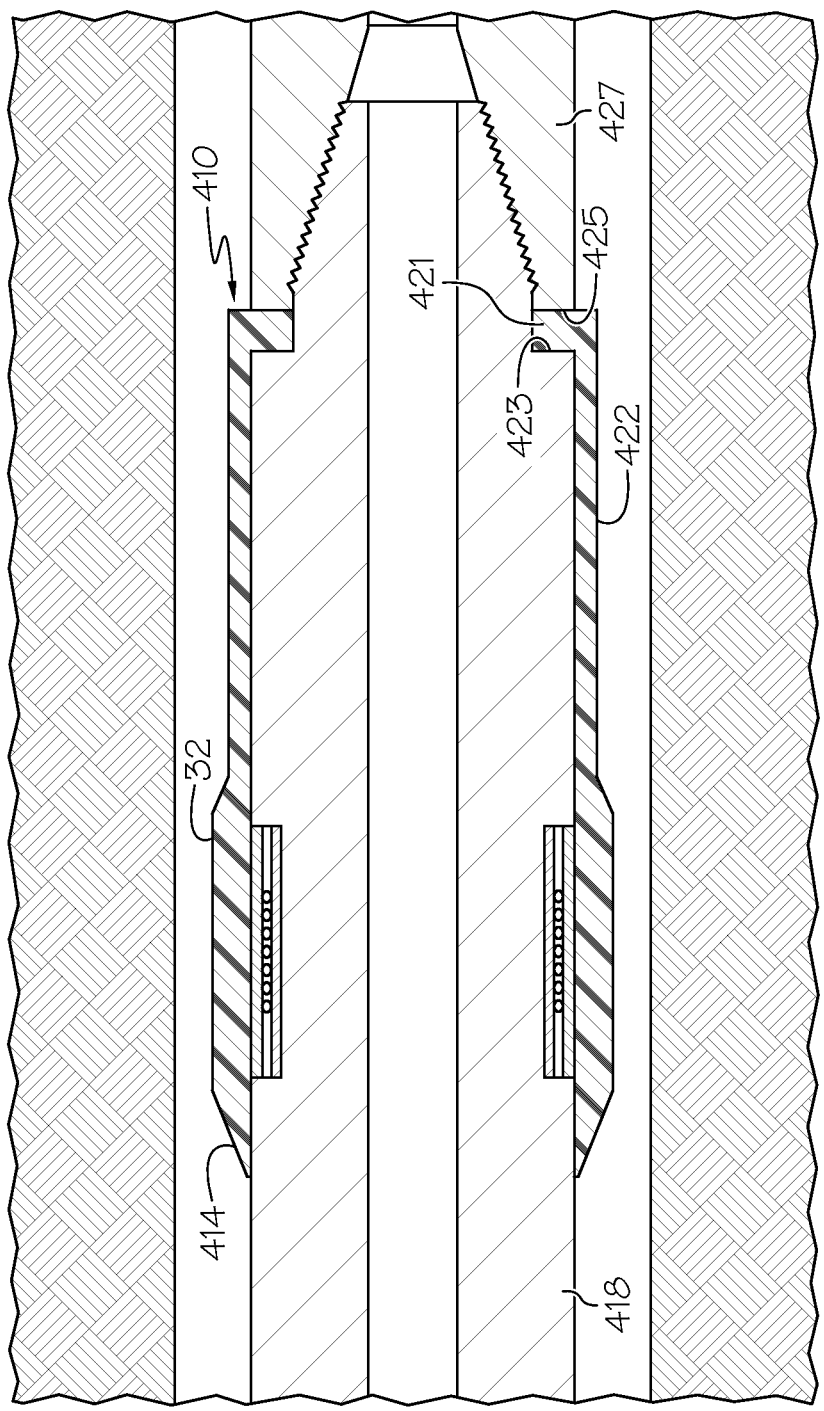
FIG. 5 depicts a cross sectional view of another embodiment of a media displacement device disclosed herein.

Referring to FIG. 5, another alternate embodiment of a media displacement device disclosed herein is illustrated at 410. Again, only the differences between the device 410 and the device 10 will be elaborated on herebelow. The device 410 differs from the device 10 in how body 414 is attached to a tool 418. The body 414 includes a shoulder 421 displaced longitudinally from the cylindrical center portion 32 via a tubular portion 422. The shoulder 421 is longitudinally compressed between a shoulder 423 on the tool 418 and a shoulder 425 on a collar 427. The collar 427 is threadably engagable with the tool 418 in a fashion such as is employed in a box and pin arrangement, for example, in the downhole industry.

Referring to FIG. 6, any of the bodies 14, 114, 214, 314 or 414 can include one or more channels 435 formed longitudinally through the maximum radial surface 42 thereof, with this embodiment including just one of the channels 435. The channel 435 can have any practical radial depth and perimetrical dimension 439. The channel 435 prevents sealing of the body 14, 114, 214, 314 or 414 to walls of the formation 26 so that fluid can flow longitudinally past the body 14, 114, 214, 314 or 414. Since the presence of the channel 439 decreases the amount of media displaced by the device 10, 110, 210, 310 and 410 the effectiveness in decreasing power loss of the electromagnetic energy transported through the media 30 in the channel 435 is also decreased. As such, the depth, perimetrical dimension 439 and the orientation of the channel 435 relative to the antenna 22 should all be considered when employing a device 10, 110, 210, 310 and 410 with the channel 439.

While the invention has been described with reference to an exemplary embodiment or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed:

1. A media displacement device comprising: a media displacement body configured to be positioned radially outwards of a logging tool, the logging tool having an antenna for transmitting electromagnetic energy to or receiving electromagnetic energy from an earth formation, the media displacement body being positioned such that electromagnetic energy transmitted or received by the logging tool travels through the media displacement body, the media displacement device causing less power loss to electromagnetic energy transmitted or received by the logging tool than the media when the media displacement body is not present, and wherein said media displacement body is composed of a material of low conductivity wherein said material is configured to produce less power loss to electromagnetic energy transmitted or received by the logging tool than the media when the media displacement body is not present.

2. The media displacement device of claim 1, sized to fill a predefined part of an annular space between the antenna and walls of a bore hole in the earth formation.

3. The media displacement device of claim 1, having a substantially constant radial thickness over a longitudinal length equal to at least that of the antenna.

4. The media displacement device of claim 1, having a radial thickness that decreases to a smaller radial thickness at longitudinal locations beyond the antenna.

5. The media displacement device of claim 1, being polymeric, ceramic, glass or combinations of polymeric, ceramic and glass.

6. The media displacement device of claim 5 including metal positioned and configured to minimize power loss of electromagnetic energy passing through the media displacement device.

7. The media displacement device of claim 6, wherein the metal is particles or longitudinally positioned strips in the media displacement device.

8. The media displacement device of claim 6, wherein the metal is selected from the group consisting of copper beryllium or other hard copper alloy.

9. The media displacement device of claim 1, having at least a portion that is cylindrical.

10. The media displacement device of claim 1, having at least one channel that extends longitudinally through a largest radial dimension of the media displacement device.

11. The media displacement device of claim 1, being attachable to the logging tool.

12. The media displacement device of claim 11, wherein attachment of the media displacement device to the logging tool is via at least one of frictional engagement, adhesion, clamping, threadable engagement and by fasteners.

13. The media displacement device of claim 1, wherein the logging tool employs at least one of nuclear magnetic resonance and inductive resistivity logging.

14. A media displacement device comprising: a media displacement body being configured to be positioned radially outwards of a logging tool, the logging tool having an antenna for transmitting electromagnetic energy to or receiving electromagnetic energy from an earth formation, the media displacement device being made of polymeric, ceramic, glass or combinations of polymeric, ceramic and glass and including metal having high electrical conductivity positioned and configured to cause less power loss to electromagnetic energy transmitted or received by the logging tool than media that the media displacement device is configured to displace.

15. A method of improving transfer of electromagnetic energy between an electromagnetic energy logging tool and an earth formation, comprising:

selecting one of a plurality of selectable electromagnetic energy logging tools having outer radial dimensions smaller than radial dimensions of a borehole at a location of the borehole where the selected electromagnetic energy logging tool will be positioned;

selecting one of a plurality of selectable media displacement devices having internal radial dimensions complementary to the outer radial dimensions of the selected electromagnetic energy logging tool and external radial dimensions less than the radial dimensions of the borehole at the location where the selected electromagnetic energy logging tool will be positioned, the selected media displacement device being made of a material that causes less power loss of electromagnetic energy transmitted or received from the selected electromagnetic energy logging tool than media that the selected media displacement device is configured to displace;

attaching the selected media displacement device to the selected electromagnetic energy logging tool; and transferring electromagnetic energy between the selected electromagnetic energy logging tool and an earth formation through the selected media displacement device.

16. The method of improving transfer of electromagnetic energy between an electromagnetic energy logging tool and an earth formation of claim 15, further comprising positioning the selected electromagnetic energy logging tool with the selected media displacement device attached thereto within a borehole.

17. The method of improving transfer of electromagnetic energy between an electromagnetic energy logging tool and an earth formation of claim 15, further comprising displacing electrically conductive media within the borehole with the selected media displacement device.

18. The method of improving transfer of electromagnetic energy between an electromagnetic energy logging tool and an earth formation of claim 15, further comprising transmitting electromagnetic energy from the selected electromagnetic energy logging tool through the selected media displacement device and into the earth formation.

19. The method of improving transfer of electromagnetic energy between an electromagnetic energy logging tool and an earth formation of claim 15, wherein the attaching includes at least one of the group consisting of frictionally engaging, clamping, longitudinally locking, adhesively attaching, screwing and threadable engaging the selected media displacement device to the selected electromagnetic energy logging tool.

* * * * *